United States Patent [19]

Minaskanian et al.

[11] Patent Number: 5,118,704
[45] Date of Patent: Jun. 2, 1992

[54] SUBSTITUTED 2-AMINOTETRALINS USEFUL AS DOPAMINERGICS

[75] Inventors: Gevork Minaskanian, Irvine; James V. Peck, Costa Mesa, both of Calif.

[73] Assignee: Whitby Research, Inc., Richmond, Va.

[21] Appl. No.: 758,887

[22] Filed: Sep. 11, 1991

Related U.S. Application Data

[63] Continuation of Ser. No. 401,060, Aug. 30, 1989.

[51] Int. Cl.$^5$ .................. A61K 31/40; C07D 209/44; C07D 209/48
[52] U.S. Cl. ..................... 514/416; 514/351; 514/357; 514/417; 514/424; 514/425; 514/427; 514/443; 514/471; 514/472; 548/472; 548/477; 548/482; 548/546; 548/550; 548/561; 548/562; 548/564; 546/330; 546/333; 546/334; 546/335; 549/55; 549/68; 549/480; 549/491
[58] Field of Search .............. 548/338, 342, 472, 473, 548/477, 478, 479, 480, 481, 543, 545, 546, 547, 550, 551, 560, 561, 562, 564; 546/333, 330, 334, 335; 549/55, 68, 74, 480, 491; 564/306; 514/415, 418, 424, 425, 427, 351, 357, 443, 469

[56] References Cited

FOREIGN PATENT DOCUMENTS 270947 6/1988 European Pat. Off. .
3718317 12/1986 Fed. Rep. of Germany .

OTHER PUBLICATIONS

Gleanon et al "Derivatives of Serotonergic Agents" J. Med. Chem 32 1921–1926 (1989).
Cecil "Medical Textbook" p. 1942, 1983.

*Primary Examiner*—Jane T. Fan
*Assistant Examiner*—Celia Chang
*Attorney, Agent, or Firm*—Richard J. Hammond

[57] ABSTRACT

Optically active or racemic compounds are provided having the formula

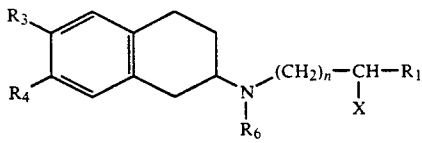

where $R_2$, $R_3$, $R_4$ and $R_6$ are defined in the specification; $R_1$ is selected from the group consisting of

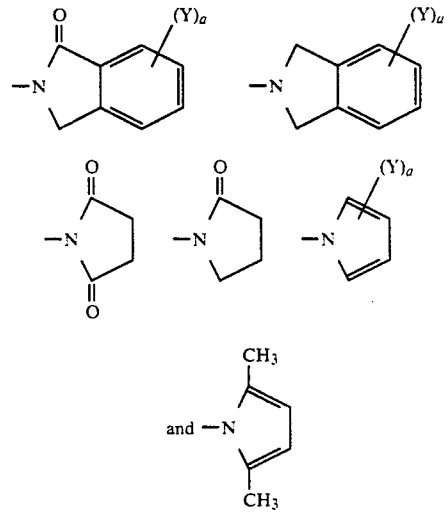

wherein Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12, preferably 1 to 6, carbon atoms, and a is an integer of from zero to 3, for instance zero to 2; and pharmaceutically acceptable salts thereof; as dopaminergics.

15 Claims, No Drawings

SUBSTITUTED 2-AMINOTETRALINS USEFUL AS DOPAMINERGICS

This is a continuation of U.S. patent application Ser. No. 07/401,060, filed Aug. 30, 1989.

BACKGROUND OF THE INVENTION

1. Field of the Invention

The invention relates generally to substituted 2-aminotetralins and to processes for preparing such compounds. More particularly, the invention relates to compounds for therapeutic use, in particular in treating disorders of the central nervous, cardiovascular and endocrine systems. The compounds of this invention are also useful for alleviating glaucoma, parkinsonism, and schizophrenia, and for inducing anorexia and weight loss in mammals.

2. Background of the Prior Art

It is known that various hydroxylated 2-aminotetralins of the general formula

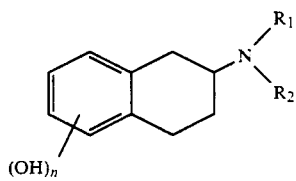

where $R_1$ and $R_2$ are saturated alkyl groups and n is 1 or 2 are dopamine receptor agonists (McDermed et al., J. Med. Chem. 18, 362 (1975); Feenstra et al., Arch. Pharmacol. 313, 213 (1980).

Many structure-activity relationship studies have been conducted to find compounds with high dopamine-receptor stimulating activity. A survey is contained in Katerinopoulos, H. E., et al., "Structure-Activity Relationships for Dopamine Analogues," Drugs of the Future, Vol. 12, No. 3, 1987, 223-253. Based upon the high activity of apomorphine, many derivatives and simplified structural analogues have been tested and found to have dopaminergic activity. For instance, some of the bicyclic analogues of dopamine, 2-amino-5,6- and 2-amino-6,7-di-hydroxytetralin, and their N-alkylated derivatives were tested and showed activity.

In addition, studies have shown that the 5-hydroxy derivatives of 2-aminotetralins possess high potency almost equivalent to that of the 5,6 catechols, with the additional advantage of increased stability, selectivity and duration of biochemical action. These studies have also shown that in bicyclic compounds the size of the two nitrogen substituents controls activity. For instance, the N-butyl and N,N-dibutyl derivatives of 2-amino-5,6-dihydroxytetralin, dopamine and norapomorphine have little or no dopaminergic activity, while analogues having at least one N-ethyl or N-n-propyl group possess high activity.

Further studies have shown that the $D_2$ receptor potency of dopamine agonists is at a maximum when one of the two N-substituents fits into a receptor niche which, because of size constraints, preferentially accommodates an n-propyl group. Conversely, activity drops off when the propyl group is replaced by the smaller groups ethyl or methyl. When the compound contains no N-substituent at least as small as n-propyl, activity is small or non-existent.

However, the structural requirements for the second N-substituent in such compounds have not been established. Consequently, the search continues for new and better N-substituents to enhance both dopamine receptor binding and activity, especially as shown by in vivo studies designed to test the dopaminergic activity of compounds, such as contralateral turning studies in 6-OH-DA-lesioned rats. See Seiler, Max P., et al., "Structure-Activity Relationships of Dopaminergic 5-Hydroxy-2-aminotetralin Derivatives with Functionalized N-Alkyl Substituents." J. Med. Chem. 1986, 29, 912–917.

The receptor site into which this second N-substituent is thought to interact appears to accommodate a wide variety of large, bulky groups having different functionalities without loss of activity. See McDermed, J. D., et al., J. Med. Chem. 1975. 18, 362; Cannon, J. G., et al., J. Med. Chem. 1977, 20, 1111; and Wikstroem, H., et al., J. Med. Chem. 1982 25, 925. However, the dopaminergic activity and potency conferred upon the compound by the choice of the second N-substituent is at present, unpredictable so that the search continues for new and better dopamine receptor agonists, especially for compounds showing a high degree of selectivity and specificity as either $D_1$ or $D_2$ receptor agonists.

SUMMARY OF THE INVENTION

There has now been discovered certain novel compounds having dopaminergic activity and having the structural formula

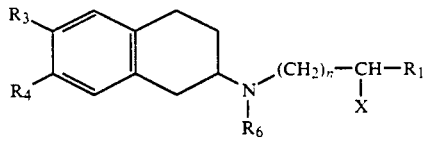

wherein $R_2$, $R_3$ and $R_4$ are each selected from the group consisting of H and OA with the provision that at least one of $R_2$, $R_3$ and $R_4$ is H, A is H or is selected from the group consisting of hydrocarbyl radicals, for example lower alkyl radicals optionally substituted with aromatic residues (i.e. methyl, ethyl, propyl, benzyl, etc.), as well as

$R_5$ is selected from the group consisting of alkyl and aromatic residues having between 1 and 12, preferably between 1 and 6, carbon atoms, for example alkyl optionally substituted with aromatic residues, and aromatic residues optionally substituted with alkyl radicals; n is an integer between 1 and 4; $R_6$ an alkyl chain comprising between 1 and 4 carbon atoms, X is selected from the group consisting of hydrogen, —$R_6$, —OH, —$OR_6$,

—$NH_2$, and —$NHR_6$. $R_1$ is selected from the group consisting of

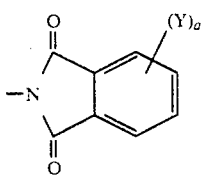

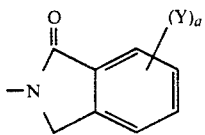

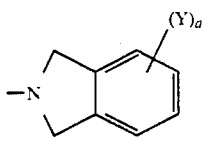

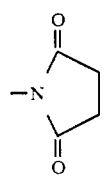

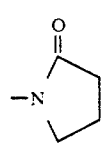

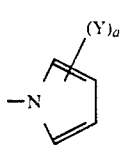

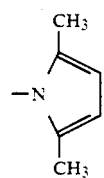

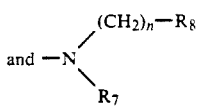

wherein Y is selected from the group consisting of hydroxy, nitro, cyano, azido, amino, acylamino, carboxyamido, trifluoro-methyl, sulfate, sufonamido, halogen, hydrocarbyl, and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3; wherein $R_7$ is selected from the group consisting of hydrogen, —$R_6$, and —$(CH_2)_m R_8$ with m being an integer of from zero to 4, and wherein $R_8$ is

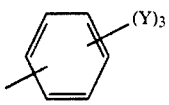

-continued

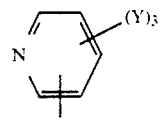

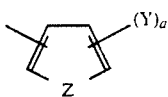

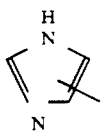

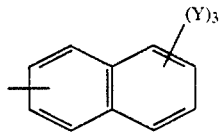

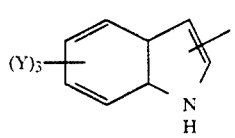

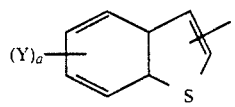

with Z being oxygen or sulfur, and pharmaceutically acceptable salts thereof.

Preferably, $R_2$ is OA and A is H.

It is essential that the compounds in the present invention be an optically active compound or racemic mixture thereof having substantial affinity and selectivity for binding to dopamine $D_2$ receptors, e.g., in a human. In particular, it is found that 6-[[3-(2,5-dimethyl-1H-pyrrol-1-yl)propyl]propylamino-5,6,7,8-tetrahydro-1-naphthalenol is especially preferred for its high affinity and selectivity for binding to dopamine $D_2$ receptors.

DETAILED DESCRIPTION OF THE INVENTION

The compounds used in the present invention are selected from the group of steroisomers or mixtures thereof of compounds having dopaminergic activity represented by the formula:

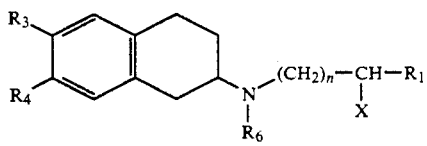

where $R_2$, $R_3$ and $R_4$ are each selected from the group consisting of H and OA with the provision that at least one of $R_2$, $R_3$ and $R_4$ is H, A is H or is selected from the group consisting of hydrocarbyl radicals, for example lower alkyl radicals, optionally substituted with aromatic residues (i.e. methyl, ethyl, propyl, benzyl, etc.),

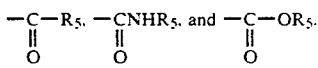

R$_5$ is selected from the group consisting of alkyl and aromatic residues having between 1 and 12, preferably between 1 and 6, carbon atoms, for example alkyl residues optionally substituted with aromatic residues and aromatic residues optionally substituted with alkyl radicals; n is an integer between 1 to 4; R$_6$ is an alkyl chain comprising between 1 and 4 carbon atoms; X is selected form the group consisting of —R$_6$, —OH, —OR$_6$,

—NH$_2$, and —NHR$_6$, R$_1$ is selected from the group consisting of

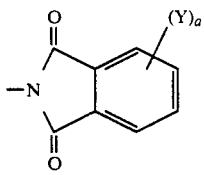

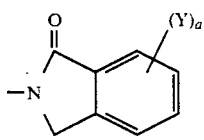

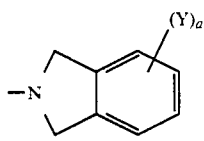

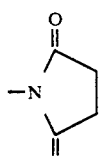

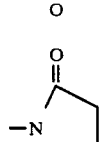

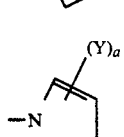

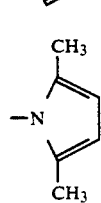

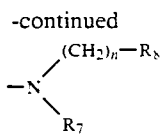

wherein Y is selected from the group consisting of hydroxy, nitro, cyano, azido, amino, acylamino, carboxyamido, trifluoromethyl, sulfate, sulfonamido, haolgen, hydrocarbyl and hetero atom-substituted hydrocarbyl radicals, wherein said heteroatoms are slected from the group consisting of halogen, nitrogen, oxygen, sulfur and phosphorus and said hydrocarbyl radicals comprise from 1 to 12, preferably 1 to 6, carbon atoms, and a is an integer of from zero to 3, for instance zero to 2; wherein R$_7$ is selected from the group consisting of hydrogen, —R$_6$, and —(CH$_2$)$_m$R$_8$ wherein R$_8$ is

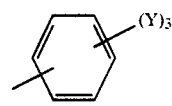

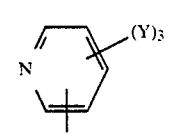

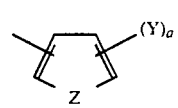

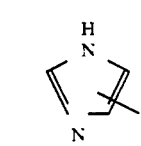

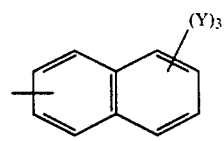

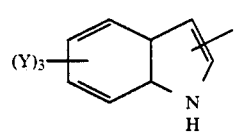

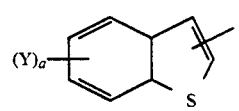

with Z being oxygen or sulfur, and pharmaceutically acceptable salts thereof.

Preferably, R$_2$ is OA and A is H.

A is preferably H or is selected from the group consisting of phenyl and alkyl radicals having from 1 to 12 carbon atoms, and more preferably R$_5$ is an alkyl or aryl radical that would serve to extend the activity of the compound in the body, for example phenyl, methyl, t-butyl, o-methylphenyl, o-, m- or p-methoxyphenyl, p-isopropyl-phenyl or nonyl.

The more preferred groups represented by $R_1$ are pyrrolyl, and isoindolyl, especially 1,3-dihydro-2H-isoindolyl and 2, 5-dimethyl pyrrolyl.

In the more preferred compounds for use in the present invention n is 2, X is hydrogen and $R_2$ is OA; and most preferably A is H and $R_6$ is propyl.

It is essential that the compounds herein be an optically active or racemic mixtures capable of binding selectively to one or more dopamine $D_2$ receptors, e.g., in a human. In particular, 2,5-dimethyl-N-propyl-N-(1,2,3,4-tetrahydro-5-hydroxy-2-naphthalenyl)-1H-pyrrole-1-propanamine is an especially preferred compound because of its high affinity and selectivity for binding to $D_2$ dopamine receptors. Due to their high affinity for binding to $D_2$ dopamine receptors, it is believed that the compounds herein will be useful in the treatment of disorders of the central nervous, cardiovascular, and endocrine systems. In particular it is believed that the compounds herein are useful in the treatment of such conditions in humans as elevated intraocular pressure, schizophrenia and parkinsonism, and for inducing anorexia and weight loss in humans and other mammals.

Particularly preferred compounds are as follows:
2,5-Dimethyl-N-propyl-N-(1,2,3,4-tetrahydro-5-methoxy-2-naphthalenyl)-1H-pyrrole-1-propanamine.
2,5-Dimethyl-N-propyl-N-(1,2,3,4-tetrahydro-5-hydroxy-2-naphthalenyl)-1H-pyrrole-1-ethanamine.
2,5-Dimethyl-N-propyl-N-(1,2,3,4-tetrahydro-5-hydroxy-2-naphthalenyl)-1H-pyrrole-1-propanamine.
2,5-Dimethyl-N-propyl-N-(1,2,3,4-tetrahydro-5-acetoxy-2-naphthalenyl)-1H-pyrrole-1-propanamine.
N-Propyl-N-(1,2,3,4-tetrahydro-5-hydroxy-2-naphthalenyl)-1H-pyrrole-1-ethanamine.
N-Propyl-N-(1,2,3,4-tetrahydro-5-hydroxy-2-naphthalenyl)-1H-pyrrole-1-propanamine.
N-Propyl-N-(1,2,3,4-tetrahydro-5-hydroxy-2-naphthalenyl)-1H-phthalimide-1-ethanamine.
N-Propyl-N-(1,2,3,4-tetrahydro-5-hydroxy-2-naphthalenyl)-1H-phthalimide-1-propanamine.
N-Propyl-N-(1,2,3,4-tetrahydro-5-benxoyloxy-2-naphthalenyl)-1H-pyrrole-1-ethanamine.
N-Propyl-N-(1,2,3,4-tetrahydro-5-benzoyloxy-2-naphthalenyl)-1H-phthalimide-1-propanamine.
6-[[3-(1,3-dihydro-2H-isoindol-2-yl)propyl]-propylamino]-5,6,7,8-tetrahydro-1-naphthalenol.
2,5-Dimethyl-N-propyl-N-(1,2,3,4-tetrahydro-5-methoxy-2-naphthalenyl)-1H-pyrrole-1-ethanamine.
N-Propyl-N-(1,2,3,4-tetrahydro-5-methoxy-2-naphthalenyl)-1H-pyrrole-1-propanamine.
N-Propyl-N-(1,2,3,4-tetrahydro-5-methoxy-2-naphthalenyl)-1H-pyrrole-1-ethanamine. N-Propyl-N-(1,2,3,4-tetrahydro-5-methoxy-2-naphthalenyl)-1H-phthalimide-1-propanamine.
N-Propyl-N-(1,2,3,4-tetrahydro-5-methoxy-2-naphthalenyl)-1H-phthalimide-1-ethanamine.
6- [[3- (1,3-dihydro-2H-isoindol-2-yl) ethyl]-propylamino]-5,6,7,8-tetrahydro-1-naphthalenol.
2,5-Dimethyl-N-propyl-N-(1,2,3,4-tetrahydro-5-benzoyloxy-2-naphthalenyl)-1H-pyrrole-1-propanamine.

The invention is further illustrated by the following examples which are illustrative of various aspects of the invention, and are not intended as limiting the scope of the inventions defined by the appended claims.

EXAMPLE 1

Preparation of 2,5-dimethyl-N-propyl-N-(1,2,3,4-tetrahydro-5-methoxy-2-naphthalenyl)-1H-pyrrole-1-propanamine A mixture of 1,2,3,4-tetrahydro-5-methoxynaphthalene (3.4 g, 0.0155 mol; prepared according to *J. Chem. Soc.*, 1965. pp 26-36), 2,5-dimethyl-1H-pyrrole-1-propanoic acid (5.18 g, 0.0155 mol; prepared according to *Chem. Commun.*, 1982, p. 800), and borane trimethylamine complex (2.26 g, 0.0310 mol) were refluxed in zylenes overnight. The cooled reaction mixture was extracted with $NaHCO_3$, the organic layer dried over $MgSO_4$, filtered and concentrated under reduced pressure. The resulting material was subjected to flash chromatography (Silica, 9:1 pet ether/EtOAc) and the product was isolated: NMR (300 MHz, $CDCl_3$) showed characteristic peaks at δ5.8 (s, 2H), 2.25 (s, 6H), 0.9 (t, 3H).

EXAMPLE 2

Preparation of 6-[[3-(2,5-dimethyl-1H-pyrrol-1-yl) propyl]propylamino-5,6,7,8-tetrahydro-1-naphthalenol The product of Example 1 was dissolved in dry dichloromethane and a solution of boron tribromide in dichloromethane was added dropwise at room temperature under nitrogen. After completion, the reaction was quenched with $NH_4OH$ and after work-up the organic layer was dried over $MgSO_4$, filtered and the concentrated residue was subjected to flash chromatography (Silica, 8:2 pet ether/EtOAc). The product was dissolved in ether and converted to a hydrochloride salt by the addition of dry ether-HCl. Anal. Calc. for $C_{22}H_{32}N_2O\bullet HCl$: C, 70.10; H, 8.82; N, 7.51. Found: C, 70.20; H, 8.91; N, 7.51. The NMR (300 MHz, $CDCl_3$) of the free base showed characteristic peaks at δ5.8 (s, 2H), 2.2 (s, 6H), 0.9 (t, 3H).

EXAMPLE 3

Preparation of 2,5-dimethyl-N-propyl-N-(1,2,3,4-tetrahydro-5-methoxy-2-naphthalenyl)-1H-pyrrole-1-ethanamine.

In Example 1, 2,5-dimethyl-1H-pyrrole-1-propanoic acid was replaced by 2,5-dimethyl-1H-pyrrole-1-acetic acid. After purification, the product showed distinct peaks at: NMR ($CDCl_3$) δ7.1 (m, 1H), 6.7 (m, 2H), 5.8 (s, 2H), 2.12 (s, 6H), 0.9 (t, 3H).

EXAMPLE 4

Preparation of 6-[[2-(2,5-dimethyl-1H-pyrrol-1-yl)ethyl]propylamino]-5,6,7,8-tetrahydro-1-naphthalenol The product of Example 3 was used as the starting material in Example 2. The purified product showed characteristic peaks at: NMR ($CDCl_3$) δ7.0 (m, 1H), 6.7 (m, 1H), 6.5 (m, 1H), 5.8 (s, 2H), 2.2 (s, 6H), 0.9 (t, 3H).

EXAMPLE 5

Preparation of N-propyl-N-(1,2,3,4-tetrahydro-5-methoxy-2-naphthalenyl)-1H-pyrrole-1-propanamine In Example 1, 2,5-dimethyl-1H-pyrrole-1-propanoic acid can be replaced by 1H-pyrrole-1-propanoic acid.

EXAMPLE 6

Preparation of
5,6,7,8-tetrahydro-6-[propyl[3-(1H-pyrrol-1-yl)propyl]amino]-1-naphthalenol The product of Example 5 can be used as the starting material in Example 2.

EXAMPLE 7

Preparation of
N-propyl-N-(1,2,3,4-tetrahydro-5-methoxy-2-naphthalenyl)-1H-pyrrole-1-ethanamine In Example 1, 2,5-dimethyl-1H-pyrrole-1-propanoic acid can be replaced by 1H-pyrrole-1-acetic acid.

EXAMPLE 8

Preparation of
5,6,7,8-tetrahydro-6-[propyl[2-(1H-pyrrol-1-yl)ethyl]amino]-1-naphthalenol The product of Example 7 can be used as the starting material in Example 2.

EXAMPLE 9

2-[3-[propyl(1,2,3,4-tetrahydro-5-methoxy-2-naphthalenyl)amino]propyl]-1H-isoindole-1,3(2H)-dione In Example 1, 2,5-dimethyl-1H-pyrrole-1-propanoic acid was replaced by 3-pthtalimidopropanoic acid. The resulting oil was subjected to flash chromatography (Silica, 95:5 pet ether/EtOAc)). Isolated product showed characteristic peaks at NMR (CDCl$_3$) δ7.8–7.6 (m, 4H), 7.1–6.6 (m, 3H), 3.8 (s, 3H), 0.9 (t, 3H).

EXAMPLE 10

Preparation of
2-[3-[propyl(1,2,3,4-tetrahydro-5-hydroxy-2-naphthalenyl)amino]propyl]-1H-isoindole-1,3(2H)-dione The product of Example 9 was combined with pyridine•HCl and heated to 200° C. in an oil bath and reaction was monitored by TLC. After completion, it was cooled, diluted with NH$_4$OH and extracted with ether. The resulting oil was purified (Silica; 9:1 pet ether/EtOAc) and characterized by NMR (300 MHz). Anal. Calc. for $C_{24}H_{28}N_2O_3$•HCl: C, 76.36; H, 6.59; N, 6.54. Found: C, 67.17; H, 6.74; N, 6.34.

EXAMPLE 11

Preparation of
6-[[3-(1,3-dihydro-2H-isoindol-2-yl)propyl]propylamino]-5,6,7,8-tetrahydro-1-napthalenol The product of Example 10 was reduced with LAH in dry THF and, after purification, the isolated compound was characterized by its HCl.salt NMR, (CD$_3$OD) δ7.8–7.5 (m, 4H), 6.95 (m, 1H), 6.6 (m, 2H), 1.0 (t, 3H).

EXAMPLE 12

Preparation of
2-[2-[propyl(1,2,3,4-tetrahydro-5-methoxy-2-naphthalenyl)amino]ethyl]-1H-isoindole-1,3(2H)-dione In Example 1, 2,5-dimethyl-1H-pyrrole-1-propanoic acid was replaced by N-phthaloylglycine. After work-up, the resulting dark oil was subjected to chromatography (Silica; pet ether/EtOAc) and product was isolated which showed distinct peaks at: NMR (CDCl$_3$) δ7.5 (m, 4H), 6.8–6.2 (m, 3H), 3.8–3.5 (m, 5H), 0.9 (t, 3H).

EXAMPLE 13

Preparation of
2-[2-[propyl(1,2,3,4-tetrahydro-5-hydroxy-2-naphthalenyl)amino]ethyl]-1H-isoindole-1,3(2H)-dione The product of Example 12 was used as the starting material in Example 10. The purified product showed characteristic peaks at: NMR (CDCl$_3$) δ7.8–7.4 (m, 4H), 7.1–6.3 (m, 3H), 3.7 (m, 2H), 0.8 (t, 3H).

EXAMPLE 14

Preparation of 6[[2-(1,3-dihydro-2H-isoindol-2-yl)ethyl]propylamino]-5,6,7,8-tetrahydro-1-naphthalenol The product of Example 13 was reduced with LAH in dry THF and, after purification, the isolated compound was characterized by its HCl.salt NMR, (CD$_3$OD) δ7.7 (m, 4H), 6.9 (m, 1H), 6.6 (m, 2H), 1.0 (t, 3H).

EXAMPLE 15

To test the selectivity and specificity of the present compounds for binding to dopamine receptors, tests were conducted using the following standard procedures.

To test binding to dopamine receptors, membranes derived from bovine caudate nuclei assay were employed. Bovine brains were obtained fresh from a local slaughterhouse. The caudate nuclei were dissected out and homogenized in Buffer A (50 mM Tris; 1 mM Na$_2$-EDTA; 5 mM KCl; 1 mM MgCl$_2$; 2 mM CaCl$_2$; pH 7.4) using a Brinkman Polytron. The homogenate was centrifuged at 40,000 × g for 20 minutes and washed once. The pellett was resuspended in Buffer A, incubated at 37° C. for 15 minutes, then centrifuged. The pellet was washed once more, resuspended to a protein concentration of 5–10 mg/ml in Buffer A and frozen at −70° C. until used.

To test binding of the compounds to $\alpha_2$-adrenergic receptors, rat cerebral cortex membranes were employed as a source of receptors. Male Sprague Dawley rats were killed by decapitation and the brains removed. The cerebral cortices were homogenized in 50 mM Tris; 2 mM MgCl$_2$ (pH 7.4), and centrifuged at 40,000 × g for 10 minutes. The pellet was washed once, resuspended in Tris/MgCl$_2$ and incubated with 8 units/ml adenosine deaminase at 37° C. for 30 minutes. The homogenate was centrifuged, washed once, resuspended to a protein concentration of 5–10 mg/ml and frozen at −70° C. until use.

The following tritiated drugs were used as radioligands for each of the receptors tested: [$^3$H]-Spiperone 21–24 Ci/mmol for D$_2$ receptors, [$^3$H]-SCH23390 75–85 Ci/mmol for D$_1$ receptors, and [$^3$H]-Para aminoclonidine 48–52 Ci/mmol for $\alpha_2$-adrenergic receptors. The radio-ligands were incubated with various concentrations of competing drug and the appropriate membrane source for periods of time as follows: 75 minutes at room temperature for D$_2$ receptors, 30 minutes at 37° C. for D$_1$ receptors, or 30 minutes at room temperature for $\alpha_2$ receptors. Specific binding was defined using 1µM butaclamol (D$_2$), 1 µM SCH23390 (D$_1$), or 1 µM yohimbine ($\alpha_2$). In addition the D$_2$ assays contained 30 nM ketaserin in order to block the binding of $^3$H-spiperone to 5HT$_2$ receptors.

The assays were terminated by filtration using a 24-port Brandell cell harvester over filters that had been previously soaked in 0.1% polyethyleneimine, and the filters were washed three times by filtration of cold buffer. The filters were then placed in 5 ml scintillation vials to which 4 ml of Beckman Ready-Protein was then added, and each vial was counted for 2 minutes in a Beckman 3801 scintillation counter calibrated for conversion of cpm to dpm. Binding data were analyzed using the Ligand program of Munson and Rodbard (1980). The results are presented as $K_i$ values if the data were best fitted to a one-site model, or as $K_H$ and $K_L$ values if a two-site model produced the better fit.

Results of the binding tests are summarized in Table 1 below:

TABLE 1

RECEPTOR AFFINITIES ($K_i$, nM)

| Example Compound | $D_2$ ($K_L$) | $D_1$($K_L$) | $a_2$ |
|---|---|---|---|
| 2 | 26 | 2700 | 1600 |
| 4 | 100 | 10000 | 1400 |
| 10 | 1260 | 3230 | 142 |
| 11 | 720 | 3000 | 1130 |
| 13 | 1260 | 14000 | 10000 |
| 14 | 52 | 4860 | 2630 |
| N-0437 | 110 | 1,000 | 190 |

This table shows high dopamine $D_2$ receptor affinities of compounds chosen from the examples above, with unexpectedly high degrees of selectivity and specificity. The compound N-0437, a potent dopamine $D_2$ agonist, is included as a reference compound for comparative purposes.

While particular embodiments of the invention have been described it will be understood of course that the invention is not limited thereto since many obvious modifications can be made and it is intended to include within this invention any such modifications as will fall within the scope of the appended claims.

We claim:

1. Optically active or racemic compounds having the formula:

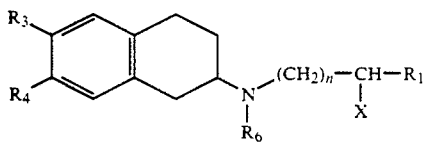

wherein $R_2$, $R_3$ and $R_4$ are each selected from the group consisting of H and OA with the provision that at least one of $R_2$, $R_3$ and $R_4$ is H, A is H or is selected form the group consisting of hydrocarbyl radicals, optionally substituted with aromatic residues selected from the group consisting of phenyl, o-methylphenyl, o-, m- or p-methoxyphenyl and p-isopropylphenyl, —C(O)—$R_5$, —C(O)NH$R_5$, and —C(O)O$R_5$, where $R_5$ is slected from the group consisting of alkyl having between 1 and 12 carbon atoms and aromatic residues selected from the group consisting of phenyl o-methylphenyl, o-, m-, or p-methoxyphenyl and isopropylphenyl; n is an integer between 1 or 4; $R_6$ is an alkyl chain having between 1 and 4 carbon atoms; X is selected from the group consisting of hydrogen —$R_6$, —OH, —O$R_6$, —OC(O)$R_6$, —NH$_2$, and —NH$R_6$, $R_1$ is selected from the group consisting of:

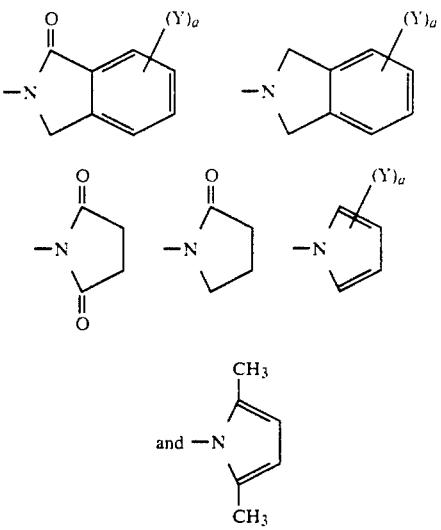

wherein Y is selected from the group consisting of hydroxy, nitro, cyano, azido, amino, carboxyamido, triflurormethyl, sulfate, sulfonamido, halogen and hydrocarbyl radicals having from 1 to 12 carbon atoms and a is an integer of from zero to 3 or pharmaceutically acceptable salts thereof.

2. The compound of claim 1 wherein A is hydrogen or a hydrocarbyl radical having between 1 and 12 carbon atoms selected from a group consisting of phenyl, alkyl and alkyl substituted with aromatic residues.

3. The compound of claim 2 wherein A is selected from the group consisting of

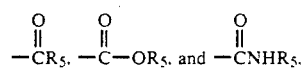

and $R_5$ is selected from the group of alkyl, alkyl substituted with aryl radicals, and aryl radicals having between 1 and 12 carbon atoms.

4. The compound of claim 1 wherein $R_5$ is selected from the group consisting of phenyl, methyl, t-butyl, o-methylphenyl, o-, m- and p-methoxyphenyl, p-isopropylphenyl, and nonyl.

5. The compound of claim 1 wherein X is selected from the group consisting of hydrogen, —$R_6$, —OH, —O$R_6$, and

$R_2$ is OA and A is H.

6. The compound of claim 5 wherein $R_1$ is selected form the group consisting of pyrrolyl, 2,5-dimethylpyrrolyl and isoindolyl; and $R_6$ is propyl.

7. The compound of claim 1 wherein X is selected from the group consisting of —NH$_2$ and —NH$R_6$, and $R_2$ is OA and A is H.

8. The compound of claim 7 wherein the $R_1$ is selected form the group consisting of pyrrolyl, 2,5-dimethylpyrrolyl and isoindolyl; and $R_6$ is propyl.

9. The compound of claim 1 where n is 2, X is hydrogen, and $R_2$ is OA.

10. The compound of claim 5 wherein Y is selected form the group consisting of hydroxy, nitro, cyano, azido, amino, and carboxyamido.

11. The compound of claim 1 wherein $R_1$ is selected from the group consisting of

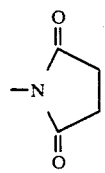

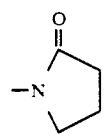

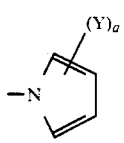

and

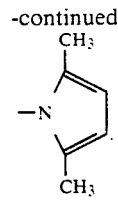

12. The compound of claim 11 wherein $R_6$ is propyl and n is 1 or 2.

13. The compound of claim 1 wherein $R_1$ is selected from the group consisting of:

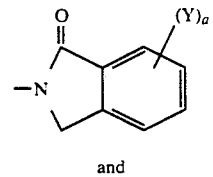

and

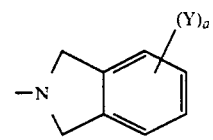

14. The compound of claim 13 wherein $R_6$ is propyl and n is 1 or 2.

15. The compound of claim 1 selected from the group consisting of 6-[[3-(2,5-dimethyl-1H-pyrrol-1-yl)propyl]propylamino-5,6,7,8-tetrahydro-1-naphthalenol, 6-[[2-(2,5-dimethyl-1H-pyrrol-1-yl)ethyl]-propylamino]-5,6,7,8-tetrahydro-1-naphthalenol, 5,6,7,8,-tetrahydro-6-[propyl[3-(1H-pyrrol-1-yl)propyl-]amino]-1-naphthalenol, 5,6,7,8-tetrahydro-6-propyl[2-(1H-pyrrol-1-yl)ethyl]amino]-1-naphthalenol, 6-[[3-(1,3-dihydro-2H-isoindol-2-yl)propyl]propyl-amino]-5,6,7,8-tetrahydro-1-naphthalenol, and 6[[2-(1,3-dihydro-2H-isoindol-2-yl)ethyl]propylamino]-5,6,7,8-tetrahydro 1-naphthalenol.

* * * * *

UNITED STATES PATENT AND TRADEMARK OFFICE
CERTIFICATE OF CORRECTION

PATENT NO. : 5,118,704

DATED : June 2, 1992

INVENTOR(S) : Gevork Minaskanian et al.

It is certified that error appears in the above-identified patent and that said Letters Patent is hereby corrected as shown below:

ON THE TITLE PAGE

Abstract, the first structural formula reads

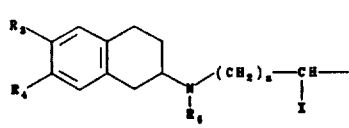    and should read    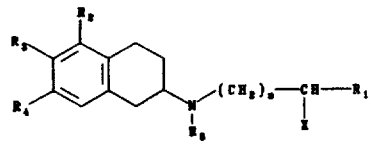

Summary of Invention, the first structural formula reads

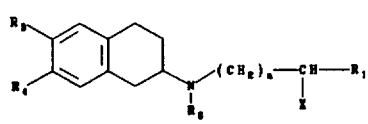    and should read    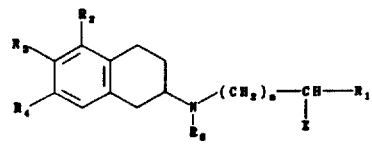

UNITED STATES PATENT AND TRADEMARK OFFICE
CERTIFICATE OF CORRECTION

PATENT NO. : 5,118,704
DATED : June 2, 1992
INVENTOR(S) : Gevork Minaskanian et al.

It is certified that error appears in the above-identified patent and that said Letters Patent is hereby corrected as shown below:

Detalied Description of the Invention, the first structural formula reads

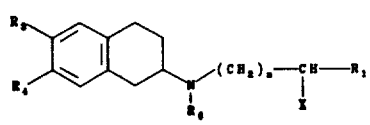 and should read 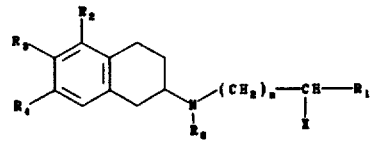

Claim 1, the first structural formula reads

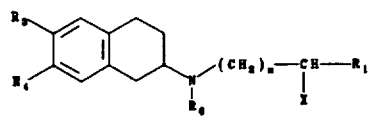 and should read 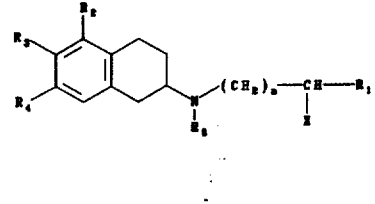

Signed and Sealed this

Twenty-fifth Day of January, 1994

Attest:

BRUCE LEHMAN

Attesting Officer     Commissioner of Patents and Trademarks